US00PP34149P3

(12) United States Plant Patent
Post

(10) Patent No.: US PP34,149 P3
(45) Date of Patent: Apr. 19, 2022

(54) ***CHRYSANTHEMUM* PLANT NAMED 'DLFFOOT5'**

(50) Latin Name: ***Chrysanthemum* X *morifolium***
Varietal Denomination: DLFFOOT5

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/395,257

(22) Filed: Aug. 5, 2021

(65) Prior Publication Data

US 2022/0046842 P1 Feb. 10, 2022

Related U.S. Application Data

(60) Provisional application No. 63/062,375, filed on Aug. 6, 2020.

(51) Int. Cl.
*A01H 5/02* (2018.01)
*A01H 6/14* (2018.01)

(52) U.S. Cl.
USPC ..... Plt./287
CPC ..... *A01H 6/1424* (2018.05)

(58) Field of Classification Search
USPC ..... Plt./287
CPC ..... A01H 6/1424
See application file for complete search history.

(56) References Cited

PUBLICATIONS

UPOV hit on *Chrysanthemum* plant named, 'DLFFOOT5', CO_A202692, dated Jun. 26, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Chrysanthemum* plant named 'DLFFOOT5', characterized by its upright plant habit; vigorous growth habit; strong dark green-colored leaves; uniform and freely flowering habit; strong upright flowering stems; pompon Santini-type inflorescences with bright yellow green-colored ray florets; resistance to *Fusarium;* relative tolerance to low production temperatures; and good postproduction longevity.

2 Drawing Sheets

Figure 1:
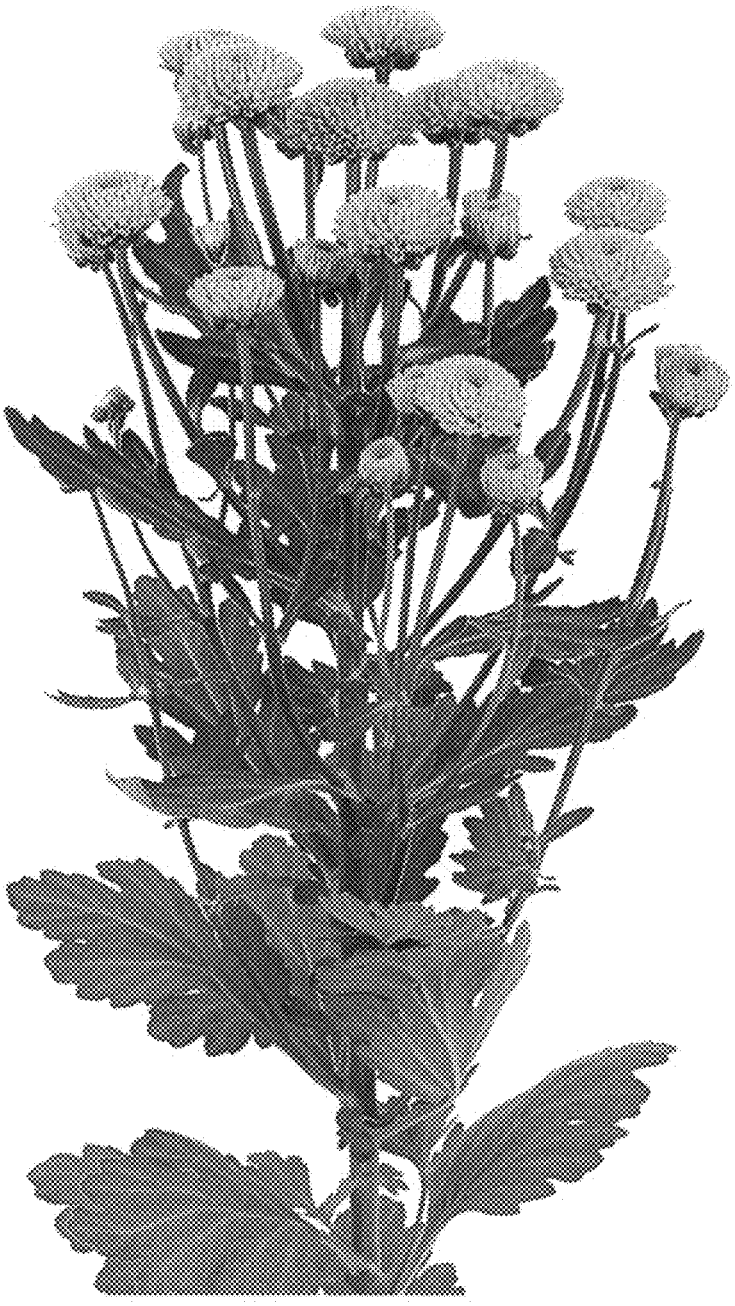

Botanical designation: *Chrysanthemum* X *morifolium.*
Cultivar denomination: 'DLFFOOT5'.

CROSS-REFERENCED TO CLOSELY-RELATED APPLICATIONS

Title: Varieties of *Chrysanthemum* Plants
Inventor/Applicant: Arie Gerard Post
Filed: Aug. 6, 2020
Ser. No. 63/062,375
Inventor/Applicant hereby claims the benefit of this provisional U.S. Patent Application.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on Jun. 26, 2020. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFFOOT5'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in December, 2011 of a proprietary selection of *Chrysanthemum* x *morifolium* identified as code number db 10061, not patented, as the female, or seed, parent with a proprietary selection of *Chrysanthemum* x *morifolium* identified as code number db 41226, not patented, as the male, or pollen, parent. The new *Chrysanthemum* plant was discovered and selected as a single flowering plant from within the progeny of the stated cross-pollination in a controlled greenhouse environment in Maasdijk, The Netherlands in August, 2012.

Asexual reproduction of the new *Chrysanthemum* plant by vegetative terminal cuttings since August, 2012 in a controlled greenhouse environment in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFFOOT5'. These characteristics in combination distinguish 'DLFFOOT5' as a new and distinct *Chrysanthemum* plant:

1. Upright plant habit; vigorous growth habit.
2. Strong dark green-colored leaves.
3. Uniform and freely flowering habit.
4. Strong upright flowering stems.
5. Pompon Santini-type inflorescences with bright yellow green-colored ray florets.
6. Resistant to *Fusarium* (*Fusarium oxysporum*).
7. Relatively tolerant to low production temperatures.
8. Good postproduction longevity.

Plants of the new *Chrysanthemum* differ primarily from plants of the female parent selection in ray floret color as ray florets of plants of the new *Chrysanthemum* are lighter yellow green in color than ray florets of plants of the female parent selection.

Plants of the new *Chrysanthemum* differ primarily from plants of the male parent selection in inflorescence shape as plants of the new *Chrysanthemum* have pompon Santini-type inflorescences whereas plants of the male parent selection have semi-double type inflorescences. In addition, ray florets apices of plants of the new *Chrysanthemum* are praemorse to emarginate whereas ray florets apices of plants of the male parent selection are mammillate.

Plants of the new *Chrysanthemum* can be compared to plants of *Chrysanthemum* X *morifolium* 'DLFGRA5', disclosed in U.S. Plant Pat. No. 30,777. In side-by-side comparisons, plants of the new *Chrysanthemum* differ primarily from plants of 'DLFGRA5' in ray floret color as ray florets of plants of the new *Chrysanthemum* are brighter yellow green than ray florets of plants of 'DLFGRA5'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFFOOT5' grown as a spray-type cut flower.

Figure 2:
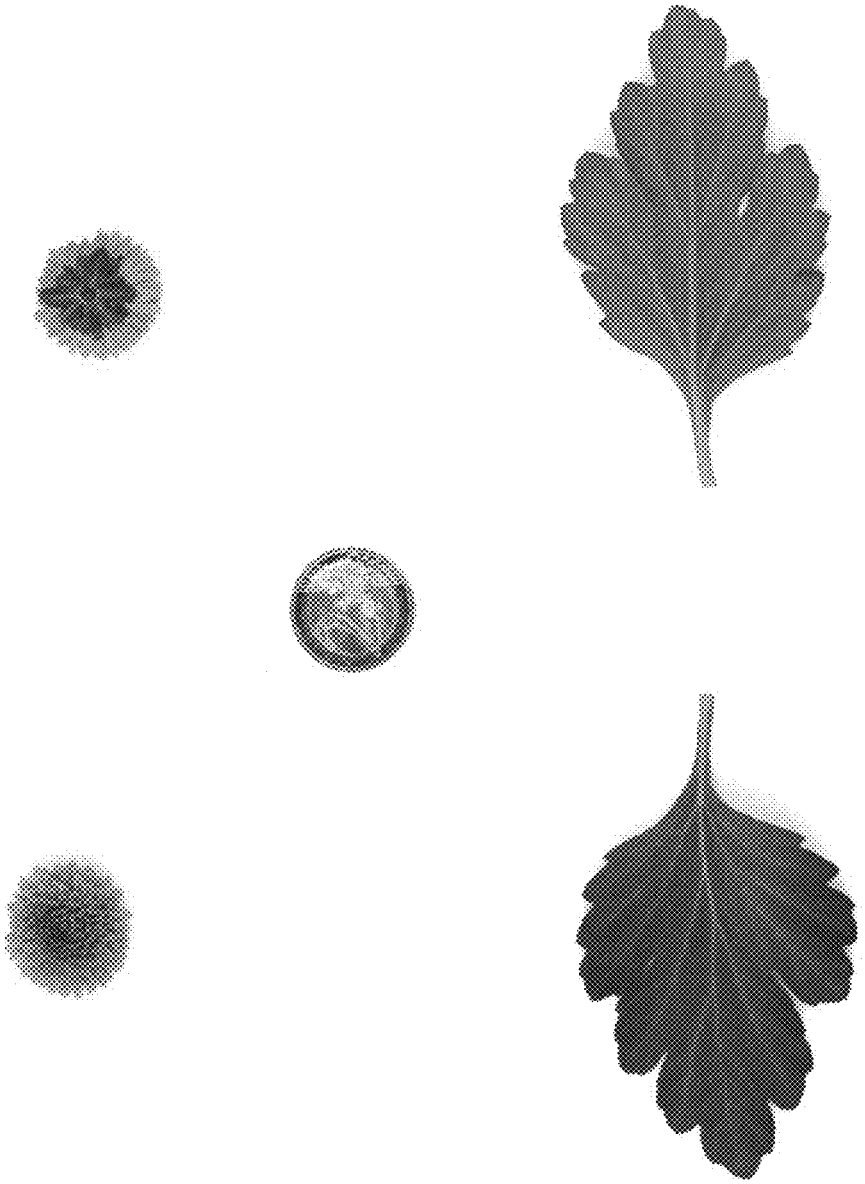

The photograph on the second sheet (FIG. 2) is a close-up view of upper (left) and lower (right) surfaces of typical leaves (bottom of photographic sheet) and inflorescences (top of photographic sheet).

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were eleven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFFOOT5'.

Parentage:

*Female, or seed, parent.*—Proprietary selection of *Chrysanthemum* x *morifolium* identified as code number db 10061, not patented.

*Male, or pollen, parent.*—Proprietary selection of *Chrysanthemum* x *morifolium* identified as code number db 41226, not patented.

Propagation:

*Type.*—Terminal vegetative cuttings.

*Time to initiate roots, summer.*—About four days at temperatures about 20° C.

*Time to initiate roots, winter.*—About six days at temperatures about 20° C.

*Time to produce a rooted young plant, summer.*—About 13 days at temperatures about 20° C.

*Time to produce a rooted young plant, winter.*—About 15 days at temperatures about 20° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous pompon Santini-type cut flower that is typically grown as a single stem spray-type; upright plant habit; vigorous growth habit and moderate to rapid growth rate.

*Plant height, soil level to top of foliar plane.*—About 57.4 cm.

*Plant height, soil level to top of inflorescence plane.*—About 60 cm.

*Plant (spray) diameter.*—About 17.8 cm.

*Flowering stem length.*—About 53.9 cm.

*Flowering stem diameter.*—About 5 mm.

*Flowering stem internode length.*—About 1.7 cm.

*Flowering stem strength.*—Strong.

*Flowering stem aspect.*—Erect.

*Flowering stem texture and luster.*—Moderately pubescent; slightly glossy.

*Flowering stem color, developing and developed.*—Close to 146B and 148A.

*Leaf description.*—Arrangement: Alternate; simple. Length: About 9.1 cm. Width: About 5.8 cm. Shape, in overall outline: Broadly ovate. Apex: Abruptly acute, minute. Base: Attenuate. Margin: Palmately lobed, coarsely crenate to dentate; sinuses convergent to parallel and medium in depth to deep. Texture and luster, upper surface: Moderately pubescent, not rugose; moderately velvety; matte. Texture and luster, lower surface: Densely pubescent, prominent venation; slightly velvety; matte. Venation pattern: Pinnate, reticulate. Color: Developing leaves, upper surface: Close to 137B to 137C. Developing leaves, lower surface: Close to between 144A and 146B. Fully developed leaves, upper surface: Close to NN137A; venation, close to 146B. Fully developed leaves, lower surface: Close to 147B; venation, close to 148C. Petioles: Length: About 1 cm. Diameter: About 2.5 mm by 3 mm. Strength: Moderately strong. Texture and luster, upper and lower surfaces: Densely pubescent; slightly glossy. Color, upper surface: Close to 146C; edges, close to 137B. Color, lower surface: Close to 147C; edges, close to 138A. Stipules: Quantity and appearance: Two leafy stipules, opposite, at the petiole attachment to the stem. Length: About 1.2 cm. Width: About 1.25 cm. Shape, in overall outline: Obovate to reniform; occasionally cleft with one to three shallow incisions distally. Texture and luster, upper surface: Moderately pubescent; matte. Texture and luster, lower surface: Densely pubescent; matte. Color, upper surface: Close to NN137A. Color, lower surface: Close to 147B.

Inflorescence description:

*Appearance.*—Pompon Santini-type inflorescence form with narrowly obovate-shaped ray florets and tubular disc florets; inflorescences borne perpendicular to peduncles and face upright; ray and disc florets develop acropetally on a capitulum.

*Fragrance.*—Faintly fragrant; typical of *Chrysanthemums*.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 48 days later when grown as a spray-type.

*Postproduction longevity.*—Good postproduction longevity; after a seven-day storage period, cut flowers will maintain good color and substance for about two weeks in an interior environment; inflorescences persistent.

*Quantity of inflorescences.*—Typically grown as a spray-type, about 61 inflorescences develop per flowering stem.

*Inflorescence size.*—Diameter, grown as a spray-type: About 3 cm. Depth (height), grown as a spray-type: About 1.6 cm. Disc diameter, grown as a spray-type: About 8 mm.

*Receptacles.*—Height: About 3 mm. Diameter: About 7 mm. Shape: Flattened globular. Color: Close to 145A to 145B.

*Inflorescence bud.*—Height: About 9 mm. Diameter: About 1.2 cm. Shape: Flattened globular. Texture and luster: Distally, smooth and glabrous; proximally, moderately pubescent; slightly glossy. Color: Developing involucral bracts, close to 137B, 137C and 138A; developing ray florets, close to 144C and 144A.

*Ray florets.*—Quantity and arrangement: About 170 arranged in about five whorls. Length: About 1.2 cm, varying between 1.1 cm and 1.3 cm. Width: About 2.5 mm, varying between 2 mm and 3 mm. Shape: Narrowly obovate; concave and slightly carinate. Apex: Praemorse to emarginate. Base: Cuneate and fused at the base. Margin: Entire; not undulate. Aspect: About 30° to 70° from vertical. Texture and luster, upper surface: Smooth, glabrous; velvety; slightly glossy. Texture and luster, lower surface: Smooth, glabrous; moderately velvety; slightly glossy. Color: When opening, upper and lower surfaces: Close to 144C. Fully opened, upper surface: Close to 145B; towards the apex, close to 144C; venation, similar to lamina colors; color does not change with subsequent development. Fully opened, lower surface: Close to 145B to 145C; towards the apex, close to 144C; venation, similar to lamina colors; color does not change with subsequent development.

*Disc florets.*—Quantity and arrangement: About 60 at the center of the receptacle. Length: About 6 mm. Diameter: About 1.25 mm. Shape: Lower 85% fused into a tube; upper 15% free. Apex: Acute. Margin, free-part: Entire. Texture and luster, inner and outer surfaces: Smooth, glabrous; glossy. Color, when opening, inner and outer surfaces: Close to 145C; distally, close to 9B and at the apex, close to N144C. Color, fully opened, inner and outer surfaces: Close to 145B to 145C; distally, close to 10A.

*Involucral bracts.*—Quantity and arrangement: About 24 arranged in about two whorls. Length: About 8 mm. Width: About 3 mm. Shape: Narrowly ovate. Apex: Narrowly obtuse. Base: Cuneate. Margin: Entire. Texture and luster, upper surface: Smooth, glabrous; glossy. Texture and luster, lower surface: Moderately pubescent; matte. Color, upper surface: Close to 137A and 147B; lateral margins, translucent and close to 156C to 156D and apical margins tinged with close to N199A. Color, lower surface: Close to 137A and 137B; lateral margins, translucent and close to 156C to 156D and apical margins tinged with close to N199A.

*Peduncles.*—Length, terminal peduncle: About 3.5 cm. Diameter, terminal peduncle: About 2.5 mm. Length, third peduncle: About 5.1 cm. Diameter, third peduncle: About 2.5 mm. Strength: Strong. Aspect, terminal peduncle: Upright. Aspect, third peduncle: About 30° from the flowering stem axis. Texture and luster: Moderately pubescent; slightly glossy. Color: Close to 138A and 143A.

*Reproductive organs.*—Androecium: Present on disc florets only. Quantity: About five per floret. Filament length: About 2 mm. Filament color: Close to 145C to 145D. Anther size: About 0.5 mm by 2 mm. Anther shape: Oblong. Anther color: Close to N144A. Pollen amount: Moderate. Pollen color: Close to 14A. Gynoecium: Present on both ray and disc florets. Quantity: One per floret. Pistil length: About 5 mm. Style length: About 4.5 mm. Style color: Close to 145B. Stigma diameter: About 1 mm. Stigma shape: Cleft to three-parted, decurrent. Stigma color: Close to N144B. Ovary color: Close to 157A.

*Seeds and fruits.*—To date, seed and fruit production have not been observed on plants of the new *Chrysanthemum.*

Pathogen & pest resistance: Plants of the new *Chrysanthemum* have been observed to be resistant to *Fusarium* Wilt (*Fusarium oxysporum* spp. *chrysanthemi* (strain FoNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFFOOT5' as illustrated and described.

* * * * *